United States Patent
Yoshimitsu et al.

(10) Patent No.: US 8,187,175 B2
(45) Date of Patent: May 29, 2012

(54) ENDOSCOPE, ENDOSCOPE APPARATUS, AND METHOD OF CONNECTING EXTERNAL EQUIPMENT TO ENDOSCOPE

(75) Inventors: Koichi Yoshimitsu, Hino (JP); Takashi Otawara, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1287 days.

(21) Appl. No.: 11/890,635

(22) Filed: Aug. 7, 2007

(65) Prior Publication Data

US 2008/0039689 A1 Feb. 14, 2008

(30) Foreign Application Priority Data

Aug. 11, 2006 (JP) ................. 2006-220465

(51) Int. Cl.
*A61B 1/00* (2006.01)
*A61B 1/04* (2006.01)
(52) U.S. Cl. ...................................... 600/132
(58) Field of Classification Search .............. 600/132; 348/75
See application file for complete search history.

(56) References Cited

U.S. PATENT DOCUMENTS

| | | | |
|---|---|---|---|
| 4,974,075 A | 11/1990 | Nakajima | |
| 5,159,446 A | 10/1992 | Hibino et al. | |
| 6,443,888 B1 * | 9/2002 | Ogura et al. | 600/132 |
| 2004/0092793 A1 | 5/2004 | Akai | |
| 2004/0134677 A1 | 7/2004 | Yamaguchi et al. | |
| 2004/0158128 A1 * | 8/2004 | Fujikawa et al. | 600/132 |

FOREIGN PATENT DOCUMENTS

| | | |
|---|---|---|
| EP | 1 600 101 A2 | 11/2005 |
| JP | 08-256977 | 10/1996 |
| JP | 3514979 | 1/2004 |
| JP | 2005-253614 | 9/2005 |
| WO | WO 01/37767 A1 | 5/2001 |

OTHER PUBLICATIONS

Office Communication dated Dec. 23, 2009 received from the European Patent Office.
Japanese Patent Abstract only of No. 2000-056238 dated Feb. 25, 2000.

\* cited by examiner

*Primary Examiner* — Philip R Smith
(74) *Attorney, Agent, or Firm* — Scully, Scott, Murphy & Presser, P.C.

(57) ABSTRACT

An endoscope according to an aspect of the invention includes an image pickup connector portion projecting from one end side of an endoscope connector and connected to a first electrical contact of a video processor, and a magnification change connector portion projecting from the other end side of the endoscope connector opposite to the one end side and connected to a second electrical contact of a magnification control device.

13 Claims, 10 Drawing Sheets

ENDOSCOPE, ENDOSCOPE APPARATUS, AND METHOD OF CONNECTING EXTERNAL EQUIPMENT TO ENDOSCOPE

This application claims benefit of Japanese Application No. 2006-220465 filed in Japan on Aug. 11, 2006, the contents of which are incorporated by this reference.

BACKGROUND OF THE INVENTION

1. Field of the Invention

The present invention relates to an endoscope including an endoscope connector connected to external equipment, an endoscope apparatus, and a method of connecting external equipment to an endoscope.

2. Description of the Related Art

As is well known, an endoscope has been widely used in such fields as the medical field and the industrial field. In the endoscope used in the medical field, an elongated insertion section of the endoscope is inserted into a body cavity of a subject to observe an organ in the body cavity. Further, if necessary, with the use of a treatment instrument inserted into a treatment instrument insertion channel of the endoscope, therapy, treatment, and so forth can be performed on tissue in the body cavity.

As an example of the configuration of the endoscope, there is a well-known configuration in which main components of the endoscope are formed by an elongated insertion section, an operation section provided consecutively to a proximal end side of the insertion section, a universal cord having one end connected to the operation section, and an endoscope connector provided to the other end of the universal cord to be connected to external equipment.

The external equipment includes, for example, a light source device which supplies a light source to the endoscope, a video processor which controls the image pickup operation of an image pickup device, such as a CCD (Charge Coupled Device), provided at the focal position of a group of lenses including an objective lens located at, for example, the distal end of the insertion section of the endoscope, and which performs image processing on a picked up endoscopic mage, a suction device which serves as a suction source in suctioning body fluid and so forth present in the body cavity through a suction channel, and a magnification control device which changes the magnification of the picked up image by advancing and retreating the group of lenses provided to the distal end of the insertion section of the endoscope.

Therefore, the endoscope is inserted with, for example, the suction channel communicating with the treatment instrument insertion channel, a light guide, and signal cables including an image pickup cable and a magnification change cable, which are connected to various devices of the external equipment in the endoscope connector.

The endoscope connector is provided with a plurality of connector portions for connecting the various devices of the external equipment to the suction channel, the light guide, the signal cables, and so forth, respectively.

As an example of the connection of the various devices of the external equipment to the plurality of connector portions of the endoscope connector, a connector portion for the light guide is first connected to the light source device, and then an electrical cable extending from the video processor (hereinafter referred to as the video processor cable) is connected to an electrical connector portion for the image pickup cable (hereinafter referred to as the image pickup connector portion).

Then, an electrical cable extending from the magnification control device (hereinafter referred to as the magnification control cable) is connected to an electrical connector portion for the magnification change (hereinafter referred to as the magnification change connector portion). Further, a tube extending from the suction device is connected to a connector portion for the suction. Thereby, the plurality of connector portions of the endoscope connector are connected to the various devices of the external equipment.

The above-described configuration in which the plurality of connector portions are provided to the endoscope connector to be connected to the various devices of the external equipment is well known, as disclosed in Japanese Patent No. 3514979, for example.

Japanese Patent No. 3514979 focuses particularly on an input-output electrical connector out of the plurality of connectors provided to the endoscope connector, and discloses a configuration in which the image pickup connector portion forming the first electrical connector and the magnification change connector portion forming the second electrical connector are provided on the same side in the endoscope connector, i.e., the image pickup connector portion and the magnification change connector portion are provided on one side of the endoscope connector.

According to the above configuration, the direction of connecting the video processor cable to the image pickup connector portion is the same as the direction of connecting the magnification control cable to the magnification change connector portion with respect to the endoscope connector. The configuration therefore enables an operator to easily connect the respective cables to the image pickup connector portion and the magnification change connector portion.

SUMMARY OF THE INVENTION

In summary, an endoscope according to an aspect of the present invention is an endoscope including an endoscope connector connected to external equipment. The endoscope includes a first electrical connector portion projecting from a first side of the endoscope connector and connected to a first electrical contact of the external equipment, and a second electrical connector portion projecting from a second side of the endoscope connector opposite to the first side and connected to a second electrical contact of the external equipment.

Further, an endoscope apparatus according to an aspect of the present invention includes the above-described endoscope and the external equipment connected to the endoscope connector of the endoscope.

Furthermore, a method of connecting external equipment to an endoscope according to an aspect of the present invention is a method of connecting external equipment to the above-described endoscope. The method includes a step of connecting the first electrical contact of the external equipment to the first electrical connector portion projecting from the first side of the endoscope connector, and a step of connecting the second electrical contact of the external equipment to the second electrical connector portion projecting from the second side of the endoscope connector opposite to the first side.

The above and other objects, features and advantages of the invention will become more clearly understood from the following description referring to the accompanying drawings.

DETAILED DESCRIPTION OF THE PREFERRED EMBODIMENT

An embodiment of the present invention will be described below with reference to the drawings. In the embodiment described below, a medical endoscope will be taken as an example of the endoscope.

Figure 1:
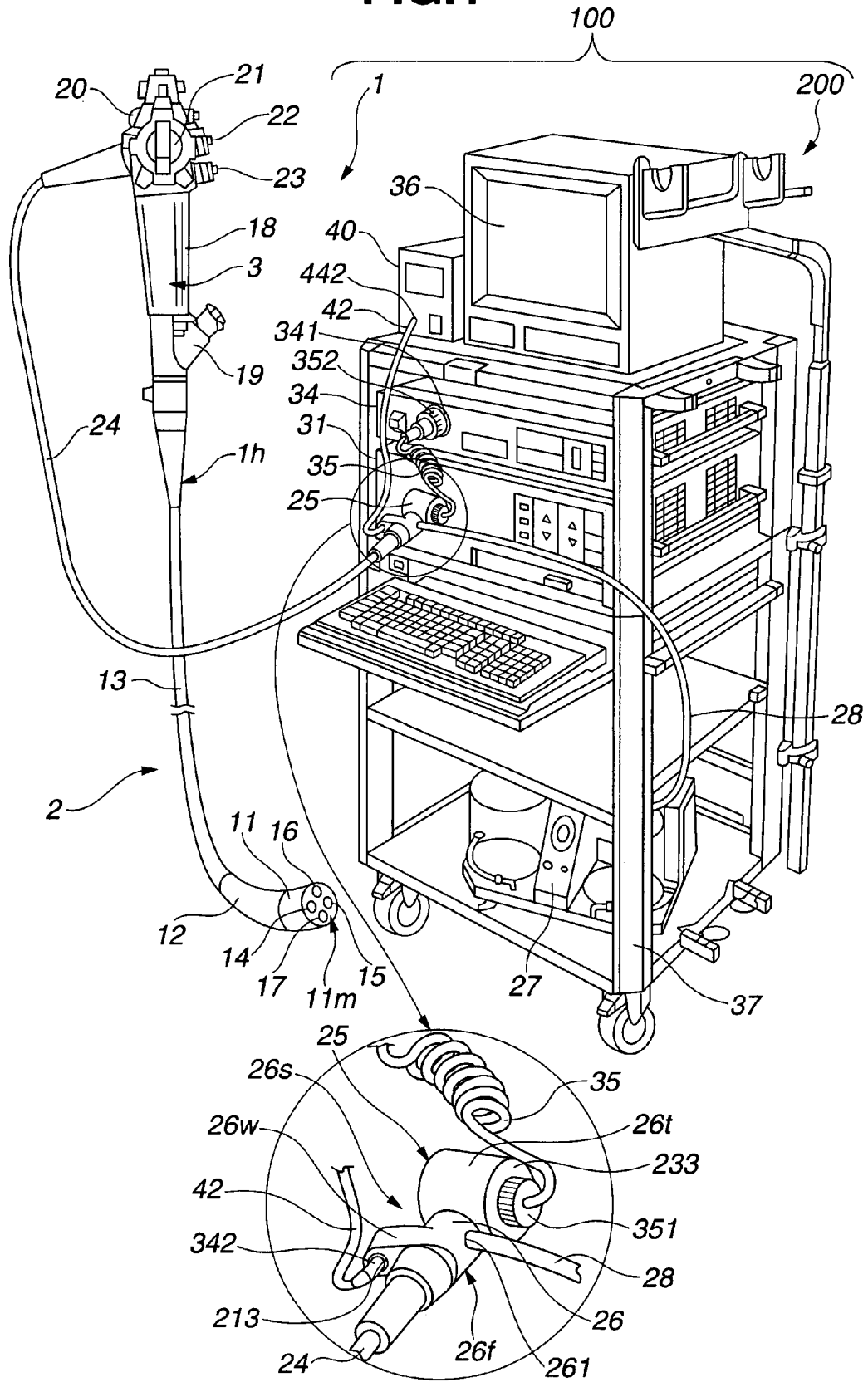
FIG. 1 is a diagram illustrating a schematic configuration of an endoscope apparatus including an endoscope according to a present embodiment.
Figure 2:
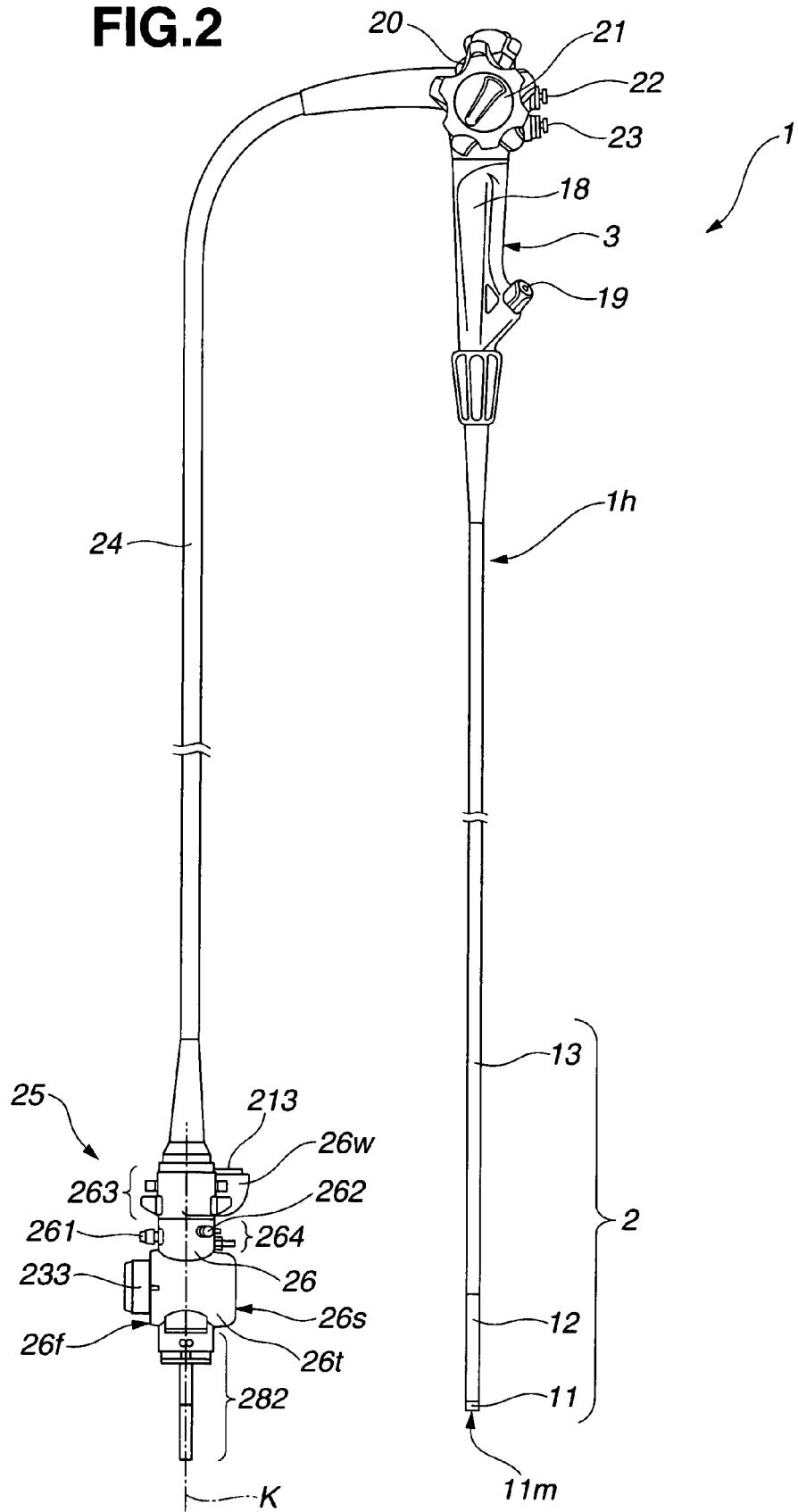
FIG. 2 is a diagram illustrating the endoscope of FIG. 1 in enlargement.
Figure 3:
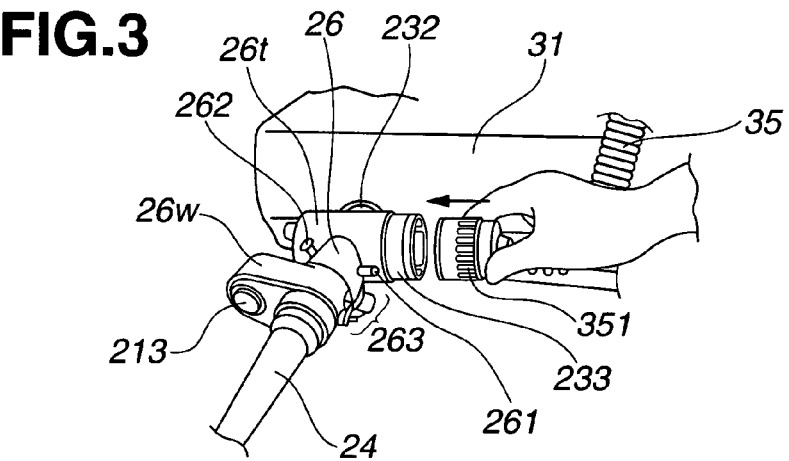
FIG. 3 is a partial perspective view illustrating a state in which a connecting portion of a video processor cable is attached to an image pickup connector portion provided to an endoscope connector of FIG. 2.
Figure 4:
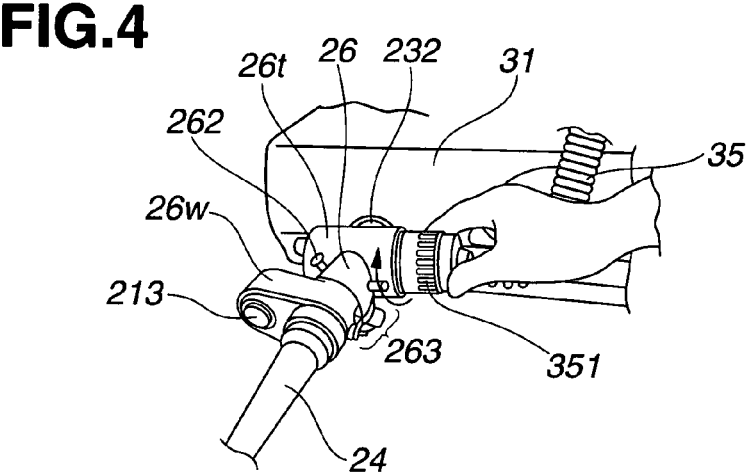
FIG. 4 is a partial perspective view illustrating a state in which the connecting portion of the video processor cable of FIG. 3 is rotated and fixed to the image pickup connector portion.

FIG. 1 is a diagram illustrating a schematic configuration of an endoscope apparatus including an endoscope according to the present embodiment. FIG. 2 is a diagram illustrating the endoscope of FIG. 1 in enlargement. FIG. 3 is a partial perspective view illustrating a state in which a connecting portion of a video processor cable is attached to an image pickup connector portion provided to an endoscope connector of FIG. 2. FIG. 4 is a partial perspective view illustrating a state in which the connecting portion of the video processor cable of FIG. 3 is rotated and fixed to the image pickup connector portion.

Figure 5:
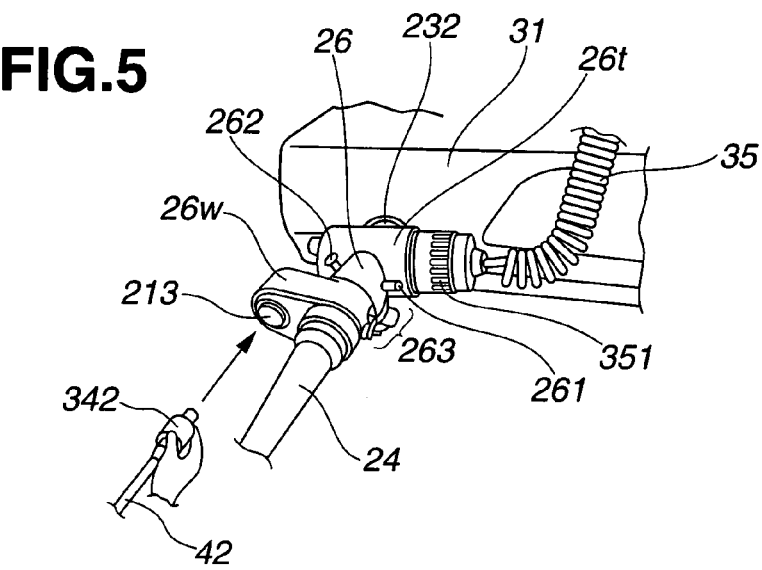
FIG. 5 is a partial perspective view illustrating a state in which a magnification control cable is attached and fixed to a magnification change connector portion provided to the endoscope connector of FIG. 2.
Figure 6:
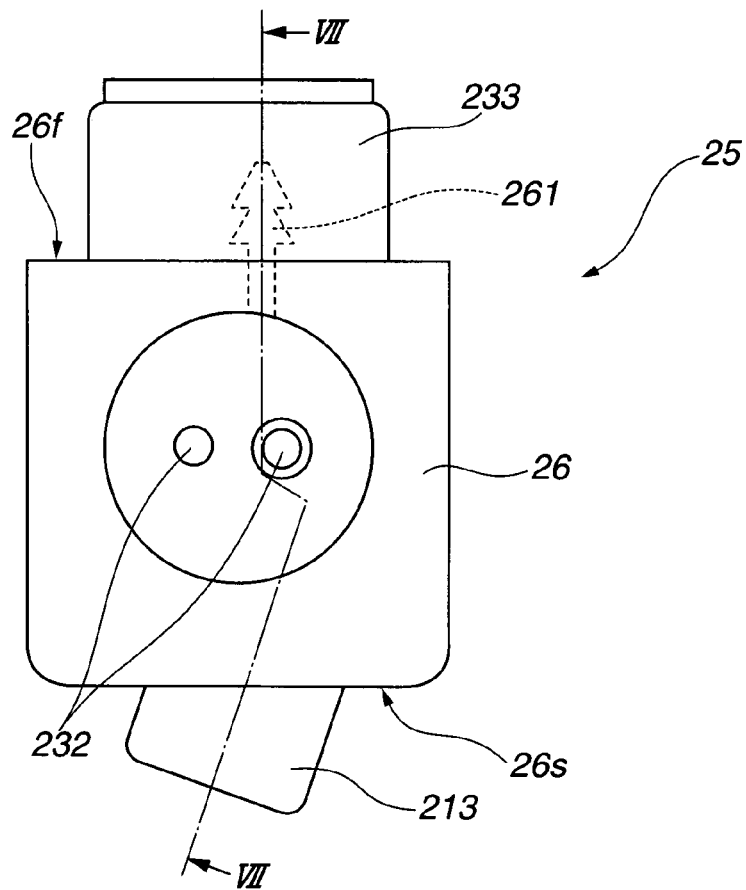
FIG. 6 is a diagram illustrating the endoscope connector of the endoscope of FIG. 2, as viewed from the side of a light source connecting connector portion.

Further, FIG. 5 is a partial perspective view illustrating a state in which a magnification control cable is attached and fixed to a magnification change connector portion provided to the endoscope connector of FIG. 2. FIG. 6 is a diagram illustrating the endoscope connector of the endoscope of FIG. 2, as viewed from the side of a light source connecting connector portion.

As illustrated in FIG. 1, main components of an endoscope apparatus 100 are formed by an endoscope 1 and external equipment 200.

As illustrated in FIGS. 1 and 2, main components of an endoscope body 1*h* of the endoscope 1 are formed by an elongated insertion section 2 inserted into a body cavity, an operation section 3 provided consecutively to a proximal end side of the insertion section 2, a universal cord 24 having one end connected to the operation section 3, and an endoscope connector 25 connected to the other end of the universal cord 24.

Main components of the insertion section 2 are formed by a distal end portion 11, a bending portion 12, and a flexible tube portion 13, which are consecutively provided in this order from the distal end.

A distal end surface 11*m* of the distal end portion 11 is provided with an objective lens 16 for condensing the light of an image of the interior of the body cavity, and an illumination lens 17 for applying illumination light into the body cavity. The distal end surface 11*m* is further provided with an air and water supply nozzle 14 for supplying liquid and gas to the objective lens 16, and an opening 15 on the side of the distal end portion 11 of a treatment instrument insertion channel functioning also as a suction channel 50 (see FIG. 7).

In addition to the above-described members and opening, the distal end surface 11*m* may be provided with, for example, a forward water supply nozzle for supplying liquid and gas into the body cavity or the like.

The distal end portion 11 is provided therein with a group of a plurality of lenses including the objective lens 16, and an advancing and retreating unit for advancing and retreating the group of lenses (both are not illustrated). At the focal position of the group of a plurality of lenses, a not-illustrated image pickup device, such as a CCD, is provided to pick up an image of the interior of the body cavity formed by the light condensed by the objective lens 16. The image pickup device may be provided in the operation section 3.

The insertion section 2 is inserted with an image pickup cable 70 (see FIG. 7) through which an image pickup signal formed by an electrical signal and an electrical signal for conveying electric power and so forth are exchanged with the image pickup device, and a not-illustrated light guide for supplying the illumination light to the illumination lens 17.

To change the magnification of the endoscopic image picked up by the image pickup device, the insertion section 2 is further inserted with a magnification change cable 60 (See FIG. 7) for supplying the advancing and retreating unit with an electrical signal for advancing and retreating the group of lenses provided in the distal end portion 11, the treatment instrument insertion channel, and air and water supply channels 51 (see FIG. 8) communicating with the air and water supply nozzle 14.

The insertion section 2 is also inserted with other electrical cables and channels, a not-illustrated bending operation wire for bending the bending portion 12, and so forth. Since the configurations of such members are well known, description thereof will be omitted. The insertion section 2 may be further inserted with a forward water supply channel communicating with the above-described forward water supply nozzle.

The operation section 3 is provided with a grasping portion 18 grasped by an operator. The grasping portion 18 is provided with a treatment instrument insertion opening 19 through which a treatment instrument, such as a forceps, is inserted and withdrawn with respect to the treatment instrument insertion channel inserted through the insertion section 2.

A proximal end side of the operation section 3 is provided with a bending operation knob 21 for performing an operation of bending the bending portion 12 in four directions of up, down, left, and right, for example, through the above-described bending operation wire, and an air and water supply switch 22 for performing an operation of causing the air and water supply nozzle 14 to discharge liquid and gas.

The proximal end side of the operation section 3 is further provided with a suction switch 23 for performing an operation of suctioning body fluid and so forth present in the body cavity from the opening 15 of the treatment instrument insertion channel formed in the distal end portion 11, and a lens moving lever 20 for performing an operation of advancing and retreating the group of lenses provided in the distal end portion 11 by supplying the advancing and retreating unit with electrical signals. The proximal end side of the operation section 3 may be also provided with other switches.

Figure 8:
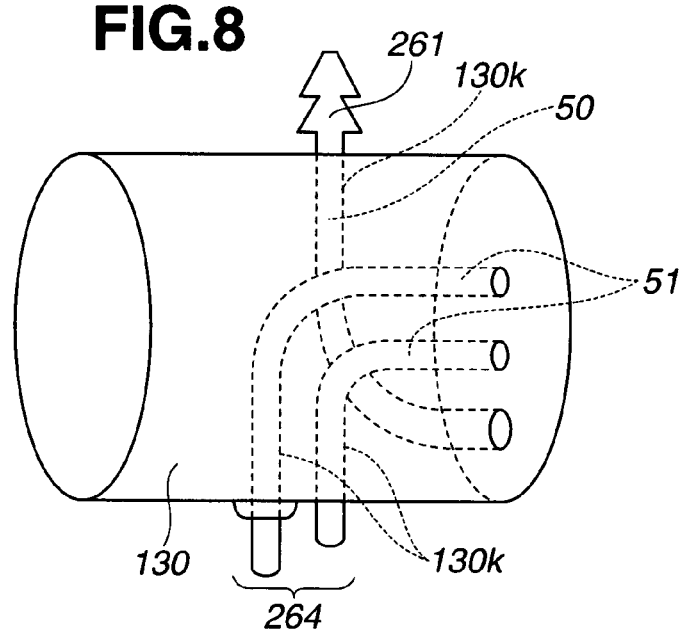
FIG. 8 is a perspective view illustrating a schematic configuration of a second shielding member of FIG. 7 with a suction cap and air and water supply caps.

The operation section 3 and the universal cord 24 are inserted with the image pickup cable 70 (see FIG. 7), the light guide, the magnification change cable 60 (see FIG. 7), the suction channel 50 (see FIG. 7) communicating with the treatment instrument insertion channel, and the air and water supply channels 51 (see FIG. 8). The operation section 3 and the universal cord 24 may be further inserted with the forward water supply channel communicating with the above-described forward water supply nozzle, other channels, and other electrical cables.

As illustrated in FIG. 2, a connector body 26 of the endoscope connector 25 is provided with a suction cap 261 communicating with the suction channel 50 (see FIG. 7), a high-frequency return terminal 262 for returning a high frequency component of a high-frequency scalpel when the high-frequency scalpel is used together with the endoscope 1, for example, a sub water supply cap 263 communicating with the forward water supply channel when the forward water supply channel is inserted through the insertion section 2, the operation section 3, and the universal cord 24, and air and water supply caps 264 communicating with the air and water supply channels 51 (see FIG. 8).

An end portion of the connector body 26 opposite to the side of the connector portion 26 connected to the universal cord 24 is provided with a light source connecting connector portion 232 (see FIG. 3), which is connectable to a later-described light source device 31. The light source connecting connector portion 232 is connected therein to one end of the above-described light guide.

Further, in a cylindrical part 26t of the connector body 26, an image pickup connector portion 233 forming a first electrical connector portion projects from one end side 26f, which forms a first side of the connector body 26 parallel to an axis (hereinafter referred to as the central axis) K set in the direction of connecting the universal cord 24 and the light source connecting connector portion 232 in FIG. 2, such that the image pickup connector portion 233 is oriented in a direction of separating from the connector body 26, as illustrated in FIGS. 2 and 6. The image pickup connector portion 233 is connected therein to one end of the later-described image pickup cable 70 (see FIG. 7).

Further, in a projecting part 26w of the connector body 26, which is provided on the side of the universal cord 24 and projects substantially perpendicular to the central axis K, a magnification change connector portion 213 forming a second electrical connector portion projects from the other end side 26s, which forms a second side of the connector body 26 opposite to the one end side 26f, such that the magnification change connector portion 213 is oriented, for example, toward the universal cord 24 connected to the connector body 26, as illustrated in FIGS. 2 and 6. That is, the magnification change connector portion 213 and the image pickup connector portion 233 project to be oriented in different directions from each other. The magnification change connector portion 213 is connected therein to one end of the later-described magnification change cable 60 (see FIG. 7).

The suction cap 261 is connected to a suction tube 28 extending from a suction device 27 of the external equipment 200, as illustrated in FIG. 1. As is known, the high-frequency return terminal 262, the sub water supply cap 263, and the air and water supply caps 264 are also connected to predetermined devices and respective tubes. The devices and tubes are not illustrated herein, and thus description thereof will be omitted.

As illustrated in FIG. 3, the light source connecting connector portion 232 is inserted in a not-illustrated connector provided to the light source device 31 of the external equipment 200, and is connected to the light source device 31.

The image pickup connector portion 233 is connected to a connecting portion 351, which is provided at the other end of the video processor cable 35. Meanwhile, one end of the video processor cable 35 is connected to a first electrical contact 341 (see FIG. 1) of a later-described video processor 34 of the external equipment 200.

The connection and fixing of the connecting portion 351 of the video processor cable 35 to the image pickup connector portion 233 is performed by attaching the connecting portion 351 to the image pickup connector portion 233, as illustrated in FIG. 3, and thereafter rotating the connecting portion 351, as illustrated in FIG. 4, to cause not-illustrated cams or the like formed to the connecting portion 351 and the image pickup connector portion 233 to engage with each other.

The magnification change connector portion 213 is connected to a connecting portion 342, which is provided at the other end of a magnification control cable 42. Meanwhile, one end of the magnification control cable 42 is connected to a second electrical contact 442 of a later-described magnification control device 40 of the external equipment 200, as illustrated in FIG. 1.

The connection and fixing of the connecting portion 342 of the magnification control cable 42 to the magnification change connector portion 213 is performed simply by attaching the connecting portion 342 to the magnification change connector portion 213, as illustrated in FIG. 5.

A detailed configuration of the interior of the endoscope connector 25 will be later described with reference to FIG. 7.

Referring back to FIG. 1, a rack 37 is mounted with the suction device 27, the light source device 31, the video processor 34, the magnification control device 40, and a monitor 36, which form the external equipment 200. The rack 37 may be mounted with other devices used for the endoscope 1.

The suction device 27 is for suctioning the body fluid and so forth present in the body cavity through the treatment instrument insertion channel, the suction channel 50 (see FIG. 7), the suction cap 261, and the suction tube 28, upon operation of the suction switch 23 of the operation section 3.

The light source device 31 is for supplying the illumination light into the body cavity through the light source connecting connector portion 232, the light guide, and the illumination lens 17.

The video processor 34 is for performing signal processing on image information transmitted from the above-described image pickup device through the image pickup cable 70 (see FIG. 7), the image pickup connector portion 233, the video processor cable 35, and the first electrical contact 341, generating a video signal, and displaying the video signal in the form of an endoscopic image on the monitor 36. The video processor 34 also supplies the image pickup device with an electrical signal conveying electric power and so forth.

The magnification control device 40 is for supplying an electrical signal conveying electric power and so forth to the advancing and retreating unit provided in the distal end portion 11 through the second electrical contact 442, the magnification control cable 42, the magnification change connector portion 213, and the magnification change cable 60 (see FIG. 7) to thereby advance and retreat the group of lenses provided in the distal end portion 11 to change the magnification of the endoscopic image displayed on the monitor 36.

Figure 9:
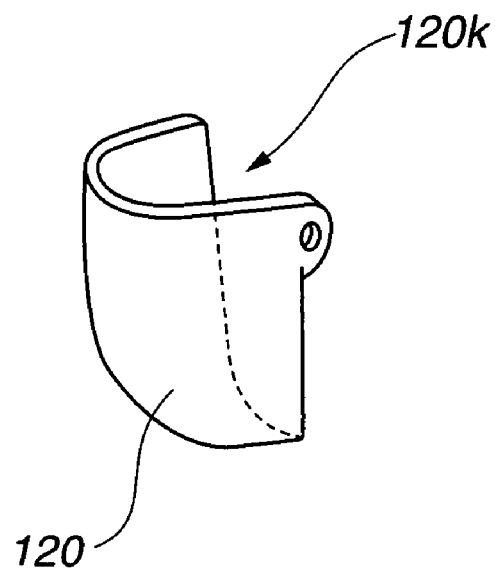
FIG. 9 is a perspective view illustrating an example of a fourth shielding member of FIG. 7.
Figure 10:
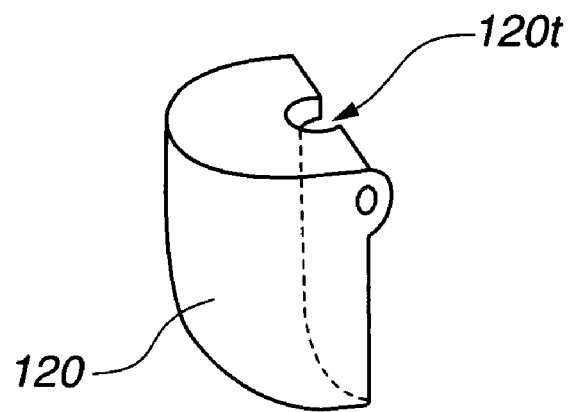
FIG. 10 is a perspective view illustrating another example of the fourth shielding member of FIG. 9.

The configuration of the interior of the endoscope connector will now be described with reference to FIGS. 7 to 10. FIG. 7 is a partial cross-sectional view along the VII-VII line of FIG. 6 illustrating the endoscope connector and a part of the universal cord. FIG. 8 is a perspective view illustrating a schematic configuration of a second shielding member of FIG. 7 with the suction cap and the air and water supply caps. FIG. 9 is a perspective view illustrating an example of a fourth shielding member of FIG. 7. FIG. 10 is a perspective view illustrating another example of the fourth shielding member of FIG. 9.

Figure 7:
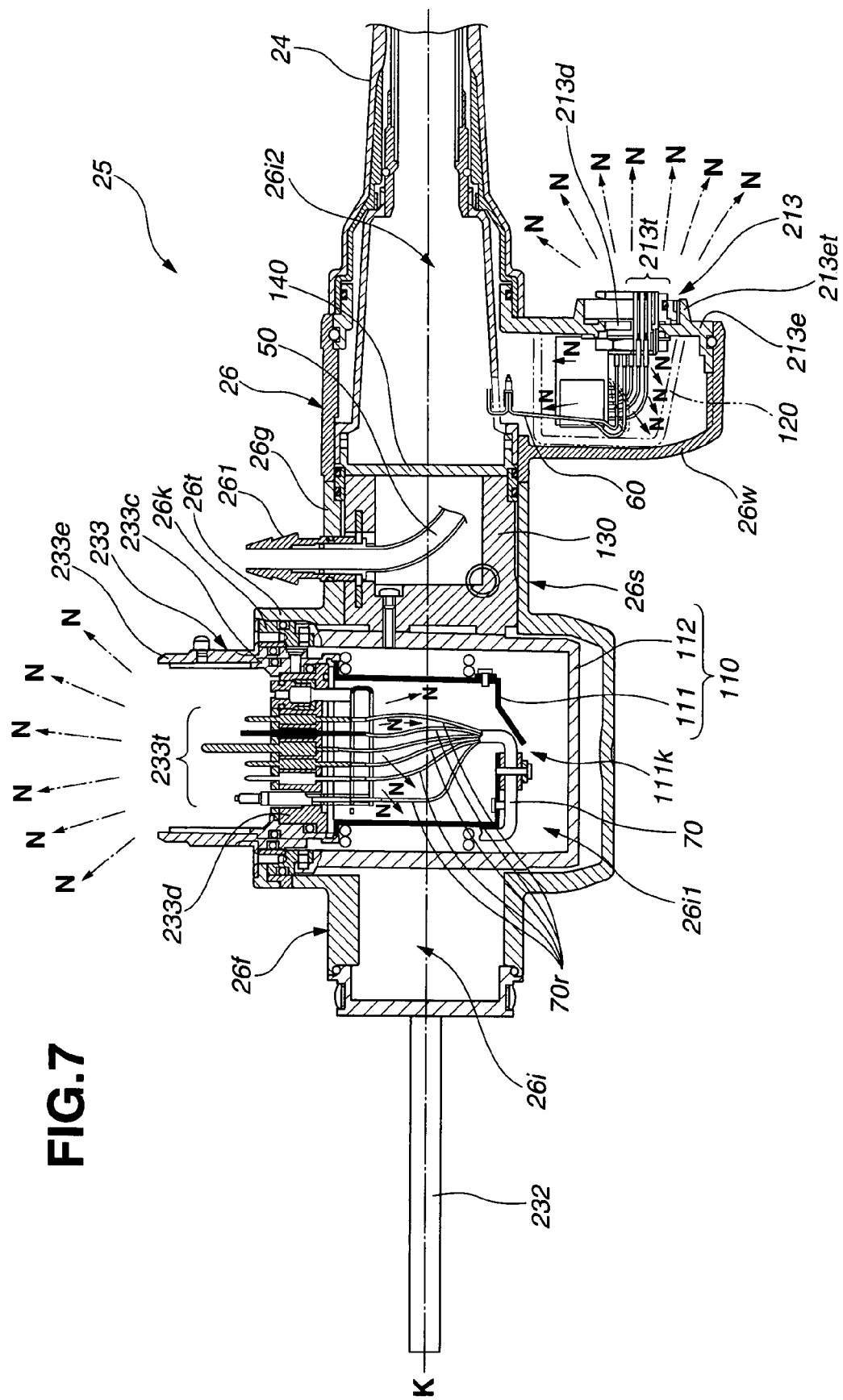
FIG. 7 is a partial cross-sectional view along the VII-VII line of FIG. 6 illustrating the endoscope connector and a part of a universal cord.

In the configuration of the interior of the endoscope connector 25 illustrated in FIG. 7, the configurations of the other components than the main components relating to the present embodiment are well known. Thus, illustration of the other members provided in the endoscope connector 25 is omitted. That is, FIG. 7 mainly illustrates the image pickup connector portion 233 and the magnification change connector portion 213.

As illustrated in FIG. 7, the connector body 26 of the endoscope connector 25 includes an external cladding member 26g including a space within an internal area 26i. The external cladding members 26g and 26w (the projecting part) form a first shielding member between the image pickup connector potion 233 and the magnification change connector portion 213 for preventing radiation noise N radiated (hereinafter referred to as leaking) from each of the connector potions 233 and 213 from entering the other one of the connector potions 233 and 213 due to the propagation of the noise from outside the endoscope connector 25, i.e., for preventing the transfer of the radiation noise N between the respective connector potions 233 and 213.

The first shielding member may be either one of the external cladding members 26g and 26w. With electrodes 213t and 233t shielded from each other by the external cladding member 26g or 26w, the transfer of the radiation noise N can be prevented even if the shielding is performed by only one of the external cladding members 26g and 26w.

The external cladding member 26g may be formed of metal or resin. If the external cladding member 26g is formed of resin, the radiation noise N radiated into the internal area 26i from the image pickup cable 70 near the image pickup connector portion 233 and the magnification change cable 60 near the magnification change connector portion 213 can be shielded from the outside, i.e., confined in the internal area 26i. Meanwhile, if the external cladding member 26g is formed of metal, the radiation noise N can be reduced to the ground level in the external cladding member 26g.

As described above, the image pickup connector portion 233 projects from the cylindrical part 26t on the one end side 26f of the external cladding member 26g. Main components of the image pickup connector portion 233 are formed by a case member 233e, an intermediate member 233c, an electrode fixing member 233d, and the plurality of electrodes 233t forming a first electrode.

The electrodes 233t are oriented in a different direction from the direction of the later-described electrodes 213t. Each of the electrodes 233t may be formed into a pin shape projecting in the direction in which the image pickup connector portion 233 projects, as illustrated in FIG. 7. If each of contacts of the connecting portion 351 provided at the other end of the video processor cable 35 connected to the image pickup connector portion 233 has a pin shape, each of the electrodes 233t may be formed into a concave shape in which the corresponding contact of the connecting portion 351 is fit.

In the inner circumference of the cylindrical part 26t on the one end side 26f of the external cladding member 26g, the cylindrical case member 233e projecting outward from the internal area 26i is fixed to the external cladding member 26g with the interposition of a fixing member 26k. Further, the electrode fixing member 233d is fixed to the inner circumference of the case member 233e with the interposition of the intermediate member 233c.

The electrode fixing member 233d is formed with a plurality of through holes passing through the electrode fixing member 233d in the direction of connecting the one end side 26f and the other end side 26s. The plurality of needle-like electrodes 233t are fit in and fixed to the plurality of through holes such that one ends of the electrodes 233t are located in the internal area 26i and the other ends of the electrodes 233t are located in the space inside the case member 233e.

The one ends of the plurality of electrodes 233t located in the internal area 26i of the connector body 26 are respectively connected to a plurality of signal lines forming the image pickup cable 70, which are exposed with an outer cover tube thereof removed.

Meanwhile, the other ends of the plurality of electrodes 233t located in the space inside the external case member 233e are fit in a plurality of concave-shaped terminals of the connecting portion 351 provided at the other end of the video processor cable 35, when the connecting portion 351 is attached to an outer circumference of the case member 233e. Thereby, the image pickup connector portion 233 and the connecting portion 351 are electrically connected to each other.

In the internal area 26i of the connector body 26, a shielding member 110 forming a cup-shaped third shielding member is provided to cover the one ends of the plurality of electrodes 233t located in the internal area 26i of the image pickup connector portion 233 and the plurality of exposed signal lines of the image pickup cable 70.

The shielding member 110 is provided between the image pickup connector portion 233 and the magnification change connector portion 213 to shield the radiation noise N radiated into the internal area 26i from the plurality of exposed signal lines of the image pickup cable 70 near the image pickup connector portion 233 and to confine the radiation noise N in a later-described first space 26i1 inside the shielding member 110. That is, the shielding member 110 is for preventing the transfer of the radiation noise N between the respective connector portions 213 and 233.

Specifically, the shielding member 110 is formed by a first cup-shaped member 111 and a second cup-shaped member 112. Each of the first cup-shaped member 111 and the second cup-shaped member 112 may be formed of metal or resin. Further, the third shielding member may be formed solely by the second cup-shaped member 112.

The first cup-shaped member 111 is fixed by screws or the like to the intermediate member 233c to cover the one ends of the plurality of electrodes 233t and the plurality of exposed signal lines of the image pickup cable 70 in a space between the inner surface of the external cladding member 26g and the first cup-shaped member 111.

A bottom portion of the first cup-shaped member 111 is formed with an opening 111k through which the image pickup cable 70 connected to the one ends of the plurality of electrodes 233t extends out from the first cup-shaped member 111.

Meanwhile, the second cup-shaped member 112 is fixed by screws or the like to the fixing member 26k to cover the first cup-shaped member 111 in a space between the inner surface of the external cladding member 26g and the second cup-shaped member 112. Although not illustrated, the second cup-shaped member 112 is also formed with an opening through which the image pickup cable 70 extends from inside the second cup-shaped member 112 into the internal area 26i.

As described above, the magnification change connector portion 213 projects from the other end side 26s of the external cladding member 26g opposite to the one end side 26f. Main components of the magnification change connector portion 213 are formed by a case member 213e, an electrode fixing member 213d, and the plurality of electrodes 213t forming a second electrode.

The electrodes 213t are oriented in a different direction from the direction of the electrodes 233t. Each of the electrodes 213t may be formed into a pin shape projecting in the direction in which the magnification change connector portion 213 projects, as illustrated in FIG. 7. If each of contacts of the connecting portion 342 provided at the other end of the magnification control cable 42 connected to the magnification change connector portion 213 has a pin shape, each of the electrodes 213t may be formed into a concave shape in which the corresponding contact of the connecting portion 342 is fit.

To the projecting part 26w, which is provided on the other end side 26s of the external cladding member 26g and projects substantially perpendicular to the central axis K, the case member 213e is fixed to be parallel to the central axis K.

The case member 213e includes a cylindrical projecting portion 213et projecting toward the universal cord 24, and a hole formed at a position opposite to the projecting portion 213et.

The inner circumference of the hole of the case member 213e is fixed with the electrode fixing member 213d formed with a plurality of through holes passing through the electrode fixing member 213d parallel to the central axis K. The plurality of needle-like electrodes 213t are fit in and fixed to the plurality of through holes such that one ends of the electrodes 213t are located in the projecting part 26w communicating with the internal area 26i of the connector body 26 and the other ends of the electrodes 213t are located in the space inside the projecting portion 213et.

The one ends of the plurality of electrodes 213t located in the projecting part 26w are respectively connected to a plurality of signal lines extending from the magnification change cable 60.

Meanwhile, the other ends of the plurality of electrodes 213t located in the space inside the projecting portion 213et are respectively fit in a plurality of concave-shaped terminals of the connecting portion 342, when the connecting portion 342 provided at the other end of the magnification control cable 42 is attached to the magnification change connector portion 213 to cover an outer circumference of the projecting portion 213et. Thereby, the connecting portion 342 and the magnification change connector portion 213 are electrically connected to each other.

In the projecting part 26w, the external cladding member 26g itself covers the one ends of the plurality of electrodes 213t and the plurality of signal lines extending from the magnification change cable 60, which are located in the internal area 26i of the magnification change connector portion 213.

Accordingly, a part of the external cladding member 26g included in the projecting part 26w forms a fourth shielding member which shields against the outside the radiation noise N radiated into the internal area 26i from the plurality of signal lines extending from the magnification change cable 60 near the magnification change connector portion 213, and which confines the radiation noise N in a later-described second space 26i2 inside the internal area 26i. That is, the external cladding member 26g is for preventing the transfer of the radiation noise N between the respective connector portions 213 and 233.

Further, a cup-shaped shielding member 120 forming a cup-shaped fourth shielding member may be provided in the projecting part 26w to cover the one ends of the plurality of electrodes 213t and the plurality of signal lines extending from the magnification change cable 60. The shielding member 120 is provided between the image pickup connector portion 233 and the magnification change connector portion 213.

The shielding member 120 is also for shielding the radiation noise N radiated into the internal area 26i from the plurality of signal lines extending from the magnification change cable 60 near the magnification change connector portion 213 and for confining the radiation noise N in the shielding member 120. That is, the shielding member 120 is for preventing the transfer of the radiation noise N between the respective connector portions 213 and 233. The shielding member 120 may be also formed of metal or resin.

The shielding member 120 is formed into a shape including an opening 120k, as illustrated in FIG. 9, through which the magnification control cable 42 extends from inside the shielding member 120 into the internal area 26i of the connector body 26. The opening is not limited to the opening 120k. Therefore, as illustrated in FIG. 10, the shielding member 120 may be formed into a shape including a hole 120*t* through which the magnification control cable 42 extends.

In the internal area 26*i* of the connector body 26, the inner circumferential surface of the external cladding member 26*g* is fixed with a disk-like connecting member 140. The connecting member 140 forms a member for holding a variety of channels and signal cables inserted in the internal area 26*i* of the connector body 26.

Therefore, the connecting member 140 is formed with through holes through which the image pickup cable 70, the magnification change cable 60, and the suction channel 50 are inserted. Although not illustrated, the connecting member 140 is further formed with through holes through which other channels, such as the air and water supply channels 51 (see FIG. 8) and the forward water supply channel, and other signal cables are inserted.

The connecting member 140 may form the fourth shielding member which shields against the outside the radiation noise N radiated into the internal area 26*i* from the plurality of signal lines extending from the magnification change cable 60 near the magnification change connector portion 213, and which confines the radiation noise N in the second space 26*i*2 of the internal area 26*i*.

Further, in the internal area 26*i* of the connector body 26, a shielding member 130 forming a second shielding member is provided to shield, i.e., confine in the first space 26*i*1 and the second pace 26*i*2 of the internal area 26*i* the radiation noise N radiated into the internal area 26*i* from the vicinity of the magnification change connector portion 213 and the image pickup connector portion 233. That is, the shielding member 130 is for preventing the transfer of the radiation noise N between the respective connector portions 213 and 233. In the internal area 26*i* of the connector body 26, the shielding member 130 is provided between the magnification change connector portion 213 and the image pickup connector portion 233.

The shielding member 130 is preferably formed of resin. If the shielding member 130 is formed of resin, the propagation of the radiation noise N radiated into the internal area 26*i* from the vicinity of the magnification change connector portion 213 and the image pickup connector portion 233 can be reliably prevented in the first space 26*i*1 and the second pace 26*i*2 of the internal area 26*i* between the magnification change connector portion 213 and the image pickup connector portion 233 due to the characteristic of the above-described resin.

As illustrated in FIG. 8, the shielding member 130 is formed with through holes 130*k* passed through by the suction channel 50 and the air and water supply channels 51. Although not illustrated, similarly to the connecting member 140, the shielding member 130 is further formed with through holes through which other channels including the forward water supply channel and signal cables including the image pickup cable 70 and the magnification change cable 60 are inserted.

In the present embodiment described above, the image pickup connector portion 233 and the magnification change connector portion 213 thus project from the one end side 26*f* and the other end side 26*s* opposite to the one end side 26*f*, respectively, in the connector body 26 of the endoscope connector 25.

Further, in the present embodiment described above, the image pickup connector portion 233 is oriented in the direction of separating from the one end side 26*f* of the connector body 26, while the magnification change connector portion 213 is oriented toward the universal cord 24. That is, the image pickup connector portion 233 and the magnification change connector portion 213 are oriented in different directions from each other.

According to the above configuration, even if the radiation noise N leaks from the image pickup connector portion 233 or the magnification change connector portion 213 after the electrical signals conveying electric power and so forth have been supplied to the connector portion 233 from the video processor 34 or to the connector portion 213 from the magnification control device 40, there is a low possibility that the radiation noise N leaking from the connector portion 233 enters the connector portion 213 or the radiation noise N leaking from the connector portion 213 enters the connector portion 233 due to the propagation of the radiation noise N from outside the endoscope connector 25. That is, the radiation noise N is prevented from being transferred between the respective connector portions 233 and 213. Further, the radiation noise N leaking from the connector portion 233 and the radiation noise N leaking from the connector portion 213 are prevented from being increased due to the synergistic effect and entering other devices of the external equipment.

The above characteristic is particularly effective in a case in which, in addition to the image pickup cable 70 for normal observation, image pickup cables extending from a plurality of image pickup units for fluorescent observation and so forth are further connected to the image pickup connector portion 233 and the radiation noise N is radiated from the respective image pickup cables, and thus in which the amount of the radiation noise N leaking from the image pickup connector portion 233 is greater than in the case in which the image pickup connector portion 233 is connected to a single image pickup cable.

Accordingly, it is possible to provide the endoscope 1 capable of implementing the EMC measure between the connector portions 213 and 233 with a simple configuration and without an increase in the level of electric power supplied to the endoscope 1 from the external equipment 200.

Further, in the present embodiment described above, the respective shielding members 110, 120, and 130 are provided in the internal area 26*i* of the connector body 26 to shield the radiation noise N radiated into the internal area 26*i* from the vicinity of the image pickup connector portion 233 and the magnification change connector portion 213, and the external cladding member 26*g* itself is formed as a shielding member for shielding the radiation noise N.

According to the above configuration, the radiation noise N radiated into the internal area 26*i* from the vicinity of the image pickup connector portion 233 and the magnification change connector portion 213 can be confined in the internal area 26*i* by the external cladding member 26*g*. In addition, the radiation noise N radiated into the internal area 26*i* from the exposed signal lines of the image pickup cable 70 in the image pickup connector portion 233 can be confined in the first internal space 26*i*1 by the shielding members 110 and 130.

Further, the radiation noise N radiated into the internal area 26*i* from the plurality of signal lines extending from the magnification change cable 60 in the magnification change connector portion 213 can be confined in the second internal space 26*i*2 by the shielding member 120, the part of the external cladding member 26*g* included in the projecting part 26*w*, and the shielding member 130.

As a result, even if the radiation noise N leaks into the inner area 26*i* of the connector body 26 from the vicinity of the image pickup connector portion 233 or the magnification change connector portion 213 after the electrical signals conveying electric power and so forth have been supplied to the connector portion 233 from the video processor 34 or to the magnification change connector portion 213 from the magnification control device 40, the radiation noise N leaking from the connector portion 233 and the radiation noise N leaking from the connector portion 213 are prevented from entering the connector portion 213 and the connector portion 233, respectively, due to the propagation of the radiation noise N in the internal area 26*i*. That is, the radiation noise N is prevented from being transferred between the respective connector portions 233 and 213.

Accordingly, it is possible to provide the endoscope 1 capable of implementing the EMC measure between the connector portions 213 and 233 with a simple configuration and without an increase in the level of electric power supplied to the endoscope 1 from the external equipment 200.

Figure 11:
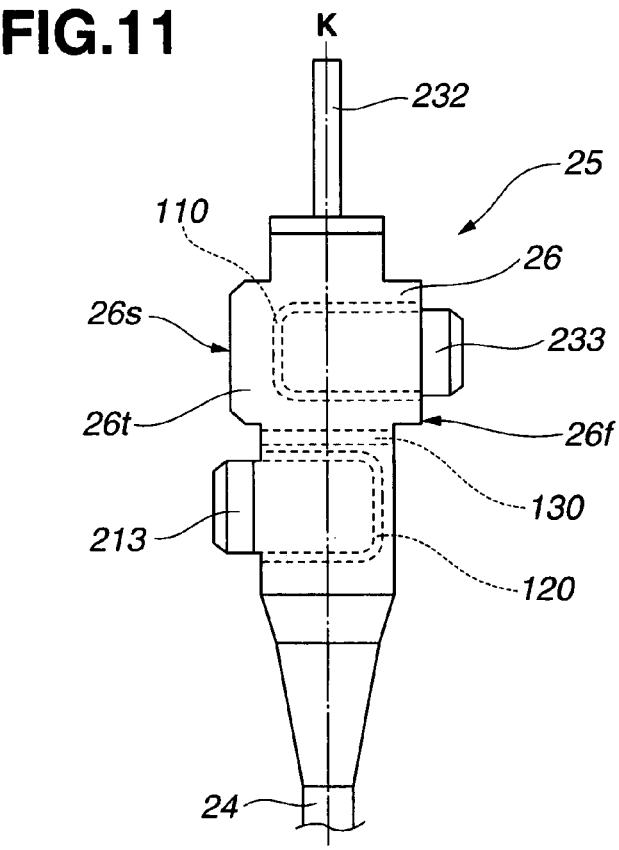
FIG. 11 is a plan view of the endoscope connector schematically illustrating a modified example of positions in the endoscope connector at which the image pickup connector portion and the magnification change connector portion are provided.

A modified example will be described below with reference to FIG. 11. FIG. 11 is a plan view of the endoscope connector schematically illustrating a modified example of the positions in the endoscope connector at which the image pickup connector portion and the magnification change connector portion are provided.

In the present embodiment described above, in the cylindrical part 26*t* on the one end side 26*f* of the connector body 26 forming one surface side across the central axis K, the image pickup connector portion 233 projects to be oriented in the direction of separating from the one end side 26*f*. Meanwhile, in the projecting part 26*w* on the other end side 26*s* of the connector body 26 forming the other surface side opposite to the one end side 26*f* across the central axis K, the magnification change connector portion 213 projects to be oriented toward the universal cord 24.

However, the configuration of the connector portions is not limited to the above. Thus, as long as the image pickup connector portion 233 and the magnification change connector portion 213 are oriented in different directions from each other, the magnification change connector portion 213 may project from the other end side 26*s* of the connector body 26 to be oriented in a direction of separating from the other end side 26*s*, as illustrated in FIG. 11.

Even if the magnification change connector portion 213 is provided to the other end side 26*s* of the connector body 26 in the above-described manner, similar effects to the effects of the present embodiment can be obtained.

Figure 12:
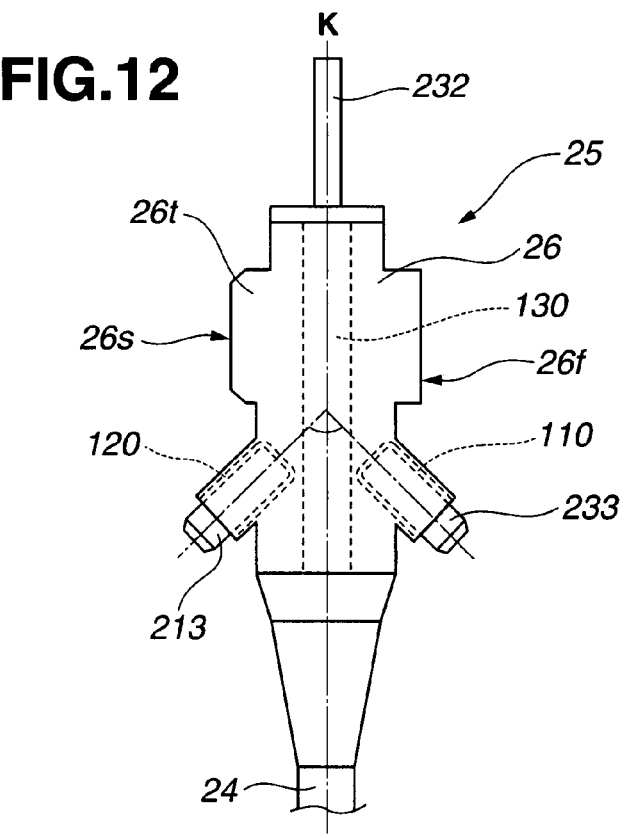
FIG. 12 is a plan view of the endoscope connector schematically illustrating a modified example wherein different positions from the positions of FIG. 11 are set as the positions in the endoscope connector at which the image pickup connector portion and the magnification change connector portion are provided.

Another modified example will be described below with reference to FIG. 12. FIG. 12 is a plan view of the endoscope connector schematically illustrating a modified example wherein different positions from the positions of FIG. 11 are set as the positions in the endoscope connector at which the image pickup connector portion and the magnification change connector portion are provided.

As illustrated in FIG. 12, the image pickup connector portion 233 and the magnification change connector portion 213 may project from respective positions on the one end side 26*f* and the other end side 26*s* of the connector body 26 to be symmetrical to each other across the central axis K.

Further, even if the image pickup connector portion 233 and the magnification change connector portion 213 project from the one end side 26*f* and the other end side 26*s*, respectively, such that the orientation direction of each of the connector portions 233 and 213 is tilted with respect to the central axis K by a set angle θ, as illustrated in FIG. 12, similar effects to the effects of the present embodiment can be obtained.

The above description similarly applies to a case in which the image pickup connector portion 233 and the magnification change connector portion 213 project from the cylindrical part 26*t* of the connector body 26.

Figure 13:
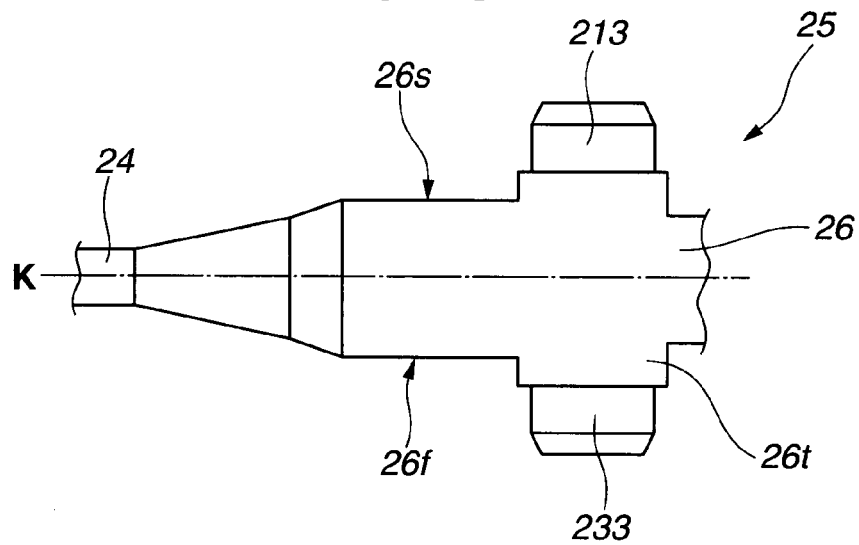
FIG. 13 is a partial plan view of the endoscope connector schematically illustrating a modified example wherein different positions from the positions of FIGS. 11 and 12 are set as the positions in the endoscope connector at which the image pickup connector portion and the magnification change connector portion are provided.

Another modified example will be described below with reference to FIG. 13. FIG. 13 is partial a plan view of the endoscope connector schematically illustrating a modified example wherein different positions from the positions of FIGS. 11 and 12 are set as the positions in the endoscope connector at which the image pickup connector portion and the magnification change connector portion are provided.

As illustrated in FIG. 13, in the connector body 26, the image pickup connector portion 233 and the magnification change connector portion 213 may project from the one end side 26*f* and the other end side 26*s*, respectively, at positions opposite to each other. Specifically, the image pickup connector portion 233 and the magnification change connector portion 213 may be provided to the one end side 26*f* and the other end side 26*s*, respectively, in the cylindrical part 26*t* to be symmetrical to each other across the central axis K.

In the above case, the image pickup connector portion 233 projects from the one end side 26*f* to be oriented in the direction of separating from the one end side 26*f*, while the magnification change connector portion 213 projects from the other end side 26*s* to be oriented in the direction of separating from the other end side 26*s*.

The above description similarly applies to a case in which the image pickup connector portion 233 and the magnification change connector portion 213 are provided to other parts of the connector body 26 than the cylindrical part 26*t*.

Figure 14:
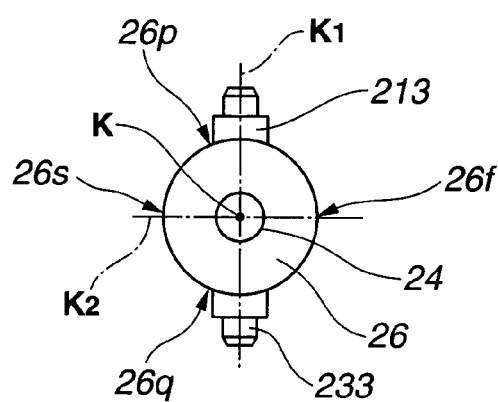
FIG. 14 is a partial end view of the endoscope connector schematically illustrating a modified example wherein different positions from the positions of FIGS. 11 to 13 are set as the positions in the endoscope connector at which the image pickup connector portion and the magnification change connector portion are provided.

Other modified examples will be described below with reference to FIGS. 14, 15, and 17. FIG. 14 is a partial end view of the endoscope connector schematically illustrating a modified example wherein different positions from the positions of FIGS. 11 to 13 are set as the positions in the endoscope connector at which the image pickup connector portion and the magnification change connector portion are provided.

Figure 15:
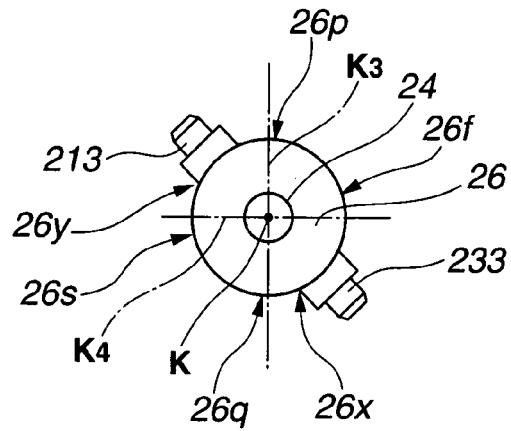
FIG. 15 is a partial end view of the endoscope connector schematically illustrating a modified example wherein different positions from the positions of FIGS. 11 to 14 are set as the positions in the endoscope connector at which the image pickup connector portion and the magnification change connector portion are provided.

Further, FIG. 15 is a partial end view of the endoscope connector schematically illustrating a modified example wherein different positions from the positions of FIGS. 11 to 14 are set as the positions in the endoscope connector at which the image pickup connector portion and the magnification change connector portion are provided. FIG. 17 is a partial end view of the endoscope connector schematically illustrating a modified example wherein different positions from the positions of FIGS. 11 to 15 are set as the positions in the endoscope connector at which the image pickup connector portion and the magnification change connector portion are provided.

In the present embodiment described above, the image pickup connector portion 233 projects from the one end side 26*f* of the connector body 26, while the magnification change connector portion 213 projects from the other end side 26*s* of the connector body 26.

However, the configuration of the connector portions is not limited to the above. Thus, as illustrated in FIG. 14, the image pickup connector portion 233 may project from a lower end side 26*q*, which forms a first side in a direction perpendicular to the central axis K and perpendicular to the direction of connecting the one end side 26*f* and the other end side 26*s*, while the magnification change connector portion 213 may project from an upper end side 26*p*, which forms a second side opposite to the first side in the direction perpendicular to the central axis K and perpendicular to the direction of connecting the one end side 26*f* and the other end side 26*s*, such that the magnification change connector portion 213 is opposite to the image pickup connector portion 233.

That is, with the lower end side 26*q* and the upper end side 26*p* divided into the first side and the second side, respectively, by an axis $K_2$ perpendicular to the central axis K, the image pickup connector portion 233 and the magnification change connector portion 213 project from the first side and the second side, respectively.

Further, as illustrated in FIG. 15, the image pickup connector portion 233 may project from a substantially intermediate position 26x between the one end side 26f and the lower end side 26q, which forms a first side, while the magnification change connector portion 213 may project from a substantially intermediate position 26y between the other end side 26s and the upper end side 26p, which forms a second side opposite to the first side, such that the magnification change connector portion 213 is opposite to the image pickup connector portion 233.

That is, with the positions 26x and 26y divided into the first side and the second side, respectively, by an axis $K_3$ or $K_4$ perpendicular to the central axis K, the image pickup connector portion 233 and the magnification change connector portion 213 project from the first side and the second side, respectively.

The central axis K is an axis passing through a substantially central position in the cross section of the connector body 26. Therefore, as illustrated in FIG. 17, with the axis $K_2$ perpendicular to the central axis K set as a central axis, the magnification change connector portion 213 and the image pickup connector portion 233 may project from the connector body 26 to be symmetrical to each other across the central axis $K_2$.

That is, the magnification change connector portion 213 may project from the substantially intermediate position 26y between the other end side 26s and the upper end side 26p of the connector body 26, while the image pickup connector portion 233 may project from a substantially intermediate position 26z between the other end side 26s and the lower end side 26q of the connector body 26 to be opposite to the magnification change connector portion 213 across the central axis $K_2$.

Figure 17:
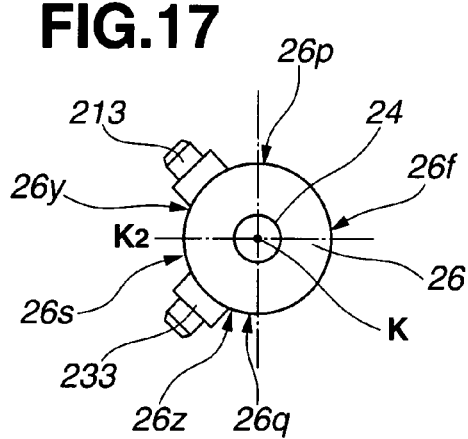
FIG. 17 is a partial end view of the endoscope connector schematically illustrating a modified example wherein different positions from the positions of FIGS. 11 to 15 are set as the positions in the endoscope connector at which the image pickup connector portion and the magnification change connector portion are provided.

As described above, similar effects to the effects of the above-described present embodiment can be obtained with the positions illustrated in FIGS. 14, 15, and 17.

Figure 16:
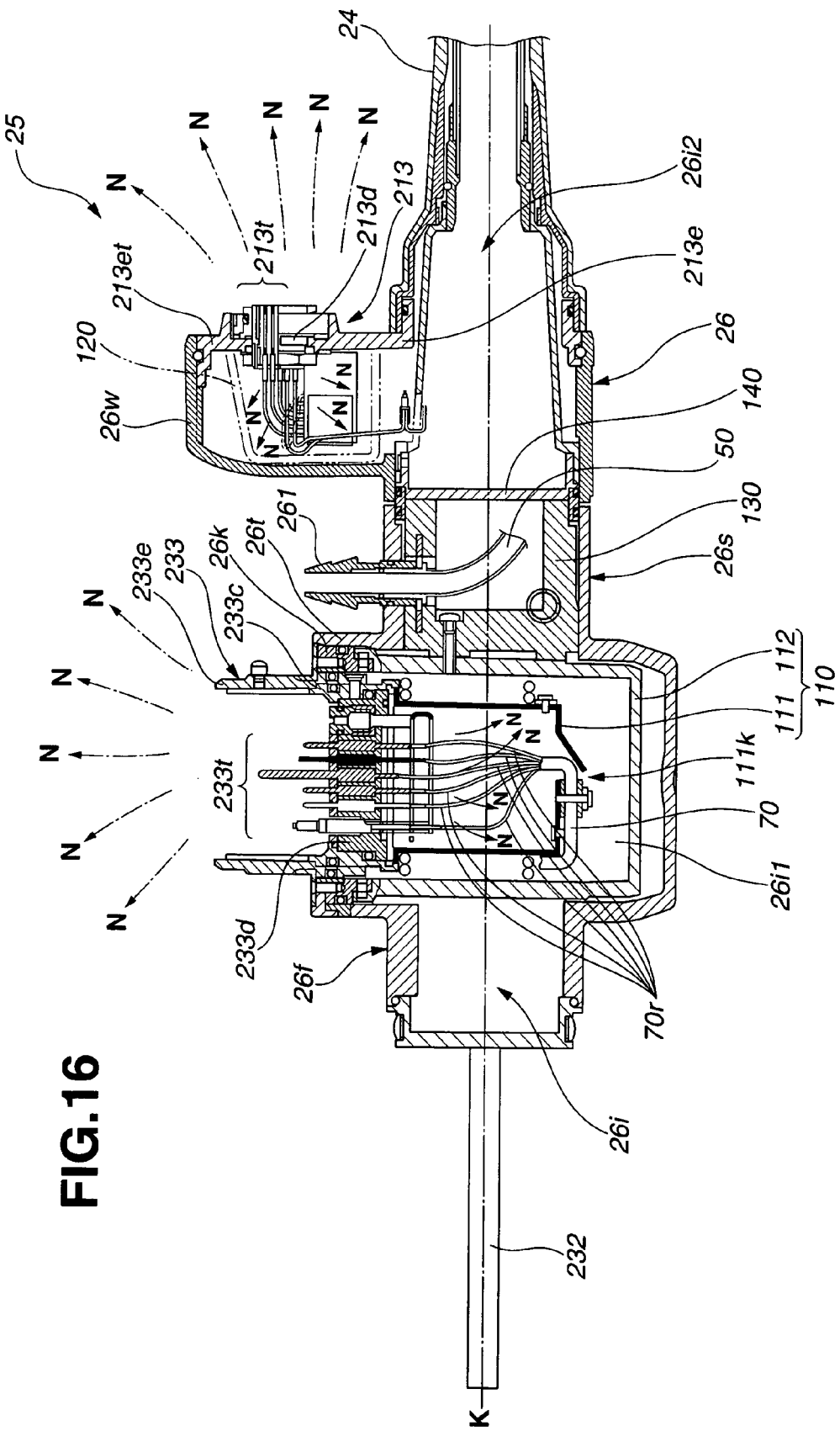
FIG. 16 is a partial cross-sectional view of the endoscope connector and the universal cord illustrating a modified example of the position at which the magnification change connector portion is provided.

Another modified example will be described below with reference to FIG. 16. FIG. 16 is a partial cross-sectional view of the endoscope connector and the universal cord illustrating a modified example of the position at which the magnification change connector portion is provided.

In the present embodiment described above, the image pickup connector portion 233 is provided to the one end side 26f of the connector body 26, while the magnification change connector portion 213 is provided to the other end side 26s.

However, the configuration of the connector portions is not limited to the above. Thus, as illustrated in FIG. 16, as long as the image pickup connector portion 233 and the magnification change connector portion 213 are different from each other in the orientation direction in which the connector portions project from the connector body 26, the projecting part 26w substantially perpendicular to the central axis K may be provided to the one end side 26f (hereinafter referred to as the first side) so that the image pickup connector portion 233 and the magnification change connector portion 213 are provided on the same side.

In the above case, the effect of preventing the transfer of the radiation noise N between the respective connector portions 213 and 233 is less than in the present embodiment. However, the connector portions 213 and 233 are different from each other in the orientation direction thereof. Thus, substantially similar effects to the effects of the present embodiment can be obtained.

Further, with the image pickup connector portion 233 and the magnification change connector portion 213 provided on the same side, the connectability of the connecting portion 351 of the video processor cable 35 to the image pickup connector portion 233 and the connectability of the connecting portion 342 of the magnification control cable 42 to the magnification change connector portion 213 are improved.

The above description similarly applies to a case in which the image pickup connector portion 233 and the magnification change connector portion 213 are provided to the other end side 26s.

Figure 18:
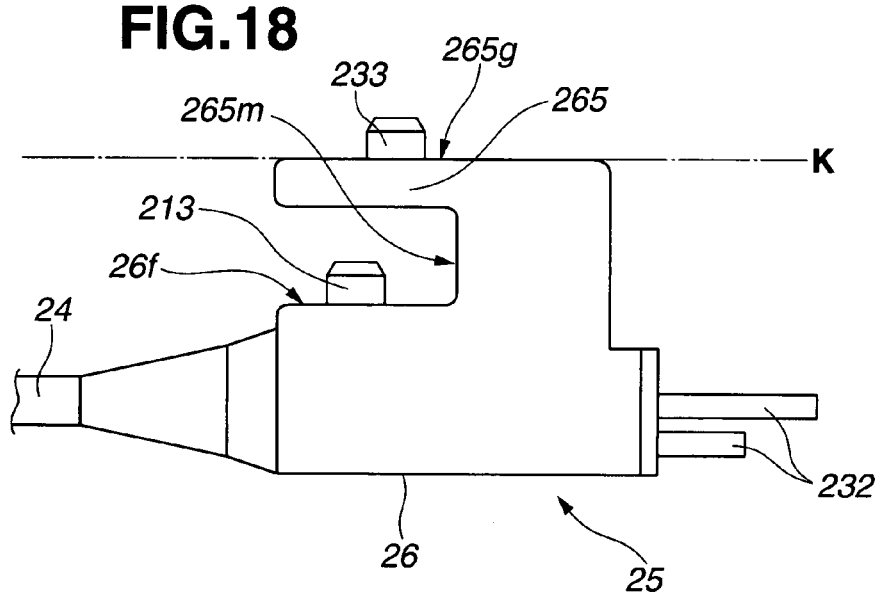
FIG. 18 is a partial plan view of the endoscope connector illustrating a modified example of the positions at which the image pickup connector portion and the magnification change connector portion are provided.
Figure 19:
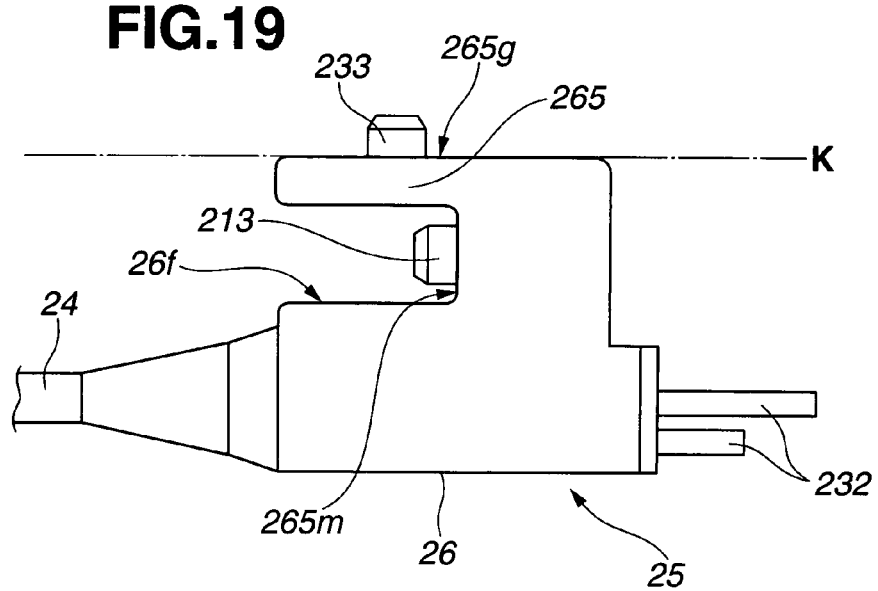
FIG. 19 is a partial plan view of the endoscope connector illustrating a modified example wherein the magnification change connector portion is provided at a different position from the position of FIG. 18.

Other modified examples will be described below with reference to FIGS. 18 and 19. FIG. 18 is a partial plan view of the endoscope connector illustrating a modified example of the positions at which the image pickup connector portion and the magnification change connector portion are provided. FIG. 19 is a partial plan view of the endoscope connector illustrating a modified example wherein the magnification change connector portion is provided at a different position from the position of FIG. 18.

In the case in which the image pickup connector portion 233 and the magnification change connector portion 213 are provided on the same side, e.g., on the first side 26f, the magnification change connector portion 213 may be provided to the first side 26f of the connector body 26, while the image pickup connector portion 233 may be provided to an external surface 265g of an L-shaped member 265 which projects outward from the first side 26f of the connector body 26 to separate from the first side 26f and which is bent to be parallel to the central axis K, as illustrated in FIG. 18.

In the above case, the L-shaped member 265 prevents the radiation noise N radiated from the respective connector portions 213 and 233 from being transferred between the connector portions 213 and 233. Therefore, substantially similar effects to the effects of the configuration illustrated in FIG. 16 can be obtained.

Alternatively, the image pickup connector portion 233 may be provided to the first side 26f of the connector body 26, while the magnification change connector portion 213 may be provided to the external surface 265g of the L-shaped member 265.

Further, as illustrated in FIG. 19, the magnification change connector portion 213 may be provided to a surface 265m of a projecting portion of the L-shaped member 265 to be oriented toward the universal cord 24, i.e., in a direction parallel to the central axis K. In such a case, too, the image pickup connector portion 233 may be provided to the surface 265m of the projecting portion of the L-shaped member 265 to be oriented toward the universal cord 24, while the magnification change connector portion 213 may be provided to the external surface 265g of the L-shaped member 265.

The above description similarly applies to a case in which the image pickup connector portion 233 and the magnification change connector portion 213 are provided to the other end side 26s (hereinafter referred to as the second side) of the connector body 26. In such a case, the L-shaped member 265 is provided to the second side 26s.

Further, in the present embodiment described above, the magnification change connector portion 213 is taken as an example of the second electrical connector portion provided to the projecting part 26w. However, the second electrical connector portion is not limited to the magnification change connector portion 213. Thus, as long as the second electrical connector portion is an input-output electrical connector portion provided to the endoscope 1, such as an electrical connector portion for a shape detection mechanism used to detect the shape of the insertion section 2, an electrical connector portion for an electric bending control device used to electrically bend the bending portion 12 of the endoscope 1, and an electrical connector portion for the image pickup used to perform fluorescent observation, for example, similar effects to the effects of the present embodiment can be obtained.

Further, in the present embodiment described above, the image pickup connector portion 233 forms the first electrical connector portion, while the magnification change connector portion 213 forms the second electrical connector portion. However, the configuration of the electrical connector portions is not limited to the above. Thus, the image pickup connector portion 233 may form the second electrical connector portion, while the magnification change connector portion 213 may form the first electrical connector portion. That is, the magnification change connector portion 213 may project from the one end side 26f, while the image pickup connector portion 233 may project from the other end side 26s. In such a case, the electrodes 233t form the second electrode, while the electrodes 213t form the first electrode.

Further, in the present embodiment described above, the image pickup connector portion 233 and the magnification change connector portion 213 are taken as examples of the two input-output electrical connector portions provided to the endoscope connector 25 of the endoscope 1. Needless to say, similar effects to the effects of present embodiment can be obtained also in the application of the EMC measure between other two input-output electrical connector portions.

Further, it is needles to say that similar effects to the effects of the present embodiment can be obtained also in the application of the EMC measure between input-output electrical connector portions provided to the operation section 3.

Further, in the present embodiment described above, the external cladding member 26g of the connector body 26 and the shielding members 110, 120, and 130 are taken as examples of the shielding member provided to the endoscope connector 25. Alternatively, the shielding member may be formed solely by the external cladding member 26g, if the object of the shielding member is limited to the prevention of the radiation noise N propagated from outside the endoscope connector 25 from being transferred between the image pickup connector portion 233 and the magnification change connector portion 213.

Further, the shielding member may be formed solely by the shielding member 130, if the object of the shielding member is limited to the prevention of the radiation noise N propagated in the internal area 26i of the connector body 26 from being transferred between the image pickup connector portion 233 and the magnification change connector portion 213.

To reliably prevent both the radiation noise N propagated from outside the endoscope connector 25 and the radiation noise N propagated in the internal area 26i of the connector body 26 from being transferred between the image pickup connector portion 233 and the magnification change connector portion 213, it is preferable to provide the shielding members 110 and 120 in the internal area 26i of the connector body 26. However, even in a configuration only including at least the external cladding member 26g and the shielding member 130, the radiation noise N propagated from outside the endoscope connector 25 and the radiation noise N propagated in the internal area 26i of the connector body 26 can be both prevented.

Further, the external cladding member 26g of the connector body 26 and the shielding members 110, 120, and 130, which form the shielding members of the present embodiment, may be all formed of resin or metal. Furthermore, as in the present embodiment in which the shielding member 130 is formed of resin, resin and metal may be separately used depending on the members.

In a case in which all of the shielding members are formed of resin, the radiation noise N may leak from the internal area 26i of the connector body 26 through the respective connector portions 233 and 213, as described above. However, the connector portions 233 and 213 are oriented in different directions from each other. In such a case, therefore, the radiation noise N can be prevented from entering the respective connector portions 233 and 213 and from being increased due to the synergistic effect, in a similar manner as in the present embodiment.

Further, in the present embodiment described above, the medical endoscope is taken as an example of the endoscope. However, the endoscope is not limited to the above. Thus, it is needless to say that the present embodiment can be applied to an industrial endoscope.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope including an endoscope connector connected to external equipment, the endoscope comprising:
a light source connecting connector to be connected to a light source device, the light source connecting connector being provided to extend from one end in an axis direction of the endoscope connector in a first direction along the axis direction
a first electrical connector portion projecting from a position adjacent to the light source connecting connector so that, on a first side of an outer circumference side portion of the endoscope connector, a first connector opening is oriented in a second direction extending from the first side so as to differ from the first direction substantially by 90 degrees, the first electrical connector portion being connected to a first electrical contact of the external equipment; and
a second electrical connector portion projecting from a position adjacent to another end in the axis direction of the endoscope connector so that, on a second side of the endoscope connector opposite to the first side of the outer circumference side portion of the endoscope connector, a second connector opening is oriented in a third direction which is substantially an opposite direction from the first direction with respect to the axis direction and which differs from the second direction substantially by 90 degrees, the second electrical connector portion being connected to a second electrical contact of the external equipment.

2. The endoscope according to claim 1,
wherein, in an endoscope body including an elongated insertion section, an operation section provided consecutively to a proximal end side of the insertion section, and a universal cord having one end connected to the operation section, the endoscope connector is connected to the other end of the universal cord.

3. The endoscope according to claim 1,
wherein the first electrical connector portion is provided with a first electrode and the second electrical connector portion is provided with a second electrode, and
wherein the first electrode and the second electrode are oriented in different projecting directions from each other.

4. The endoscope according to claim 1,
wherein, between the first electrical connector portion and the second electrical connector portion of the endoscope connector, a shielding member is provided to prevent the transfer of noise radiated from the first electrical connector portion and the second electrical connector portion.

5. The endoscope according to claim 4,
wherein the endoscope connector includes an external cladding member forming therein an internal space, and
wherein the shielding member is formed by at least a first shielding member formed by the external cladding member.

6. The endoscope according to claim 5,
wherein the shielding member further includes a second shielding member for shielding between the first electrical connector portion and the second electrical connector portion in the internal space.

7. The endoscope according to claim 6,
wherein the shielding member further includes
a third shielding member for covering, in the internal space, at least a part of the internal space included in the first electrical connector portion, and
a fourth shielding member for covering, in the internal space, at least a part of the internal space included in the second electrical connector portion.

8. The endoscope according to claim 7,
wherein the third shielding member includes at least a first cup-shaped member for covering the part of the internal space included in the first electrical connector portion, and a second cup-shaped member for covering the first cup-shaped member.

9. The endoscope according to claim 6,
wherein at least the second shielding member is formed of resin.

10. The endoscope according to claim 6,
wherein the endoscope connector is inserted with a channel and a cable which extend over at least one of a range from the endoscope connector to an operation section through a universal cord and a range from the endoscope connector to a distal end of an insertion section through the universal cord, the operation section, and the insertion section, and
wherein the second shielding member is formed with through holes through which the channel and the cable are inserted.

11. The endoscope according to claim 4,
wherein the shielding member is formed of at least one of metal and resin.

12. An endoscope apparatus comprising:
the endoscope according to claim 1; and
the external equipment connected to the endoscope connector of the endoscope.

13. A method of connecting external equipment to an endoscope, the method comprising:
a step of connecting the first electrical contact of the external equipment to the first electrical connector portion projecting from a position adjacent to the light source connecting connector so that, on the first side of the outer circumference side portion of the endoscope connector of the endoscope according to claim 1, a first connector opening is oriented in the second direction extending from the first side so as to differ from the first direction substantially by 90 degrees; and
a step of connecting the second electrical contact of the external equipment to the second electrical connector portion projecting from a position adjacent to another end in the axis direction of the endoscope connector so that, on the second side opposite to the first side of the outer circumference side portion of the endoscope connector, a second connector opening is oriented in the third direction.

* * * * *